United States Patent [19]

Roger

[11] Patent Number: 4,986,826

[45] Date of Patent: Jan. 22, 1991

[54] METHOD AND APPARATUS FOR REMOVING PROSTHETIC CEMENT

[76] Inventor: Gregory J. Roger, 5 Kent Street, Collaroy, Australia, 2097

[21] Appl. No.: 393,909

[22] PCT Filed: Jan. 28, 1988

[86] PCT No.: PCT/AU88/00019

§ 371 Date: Sep. 20, 1989

§ 102(e) Date: Sep. 20, 1989

[87] PCT Pub. No.: WO88/05645

PCT Pub. Date: Aug. 11, 1988

[30] Foreign Application Priority Data

Jan. 29, 1987 [AU] Australia ............................... PI0090

[51] Int. Cl.$^5$ .............................................. A61B 17/14
[52] U.S. Cl. ........................................ 606/82; 606/99; 606/177
[58] Field of Search ..................... 606/99, 92, 102, 86, 606/104, 82, 84, 79, 176–179

[56] References Cited

U.S. PATENT DOCUMENTS 4,502,484 3/1985 Giampapa et al. .................. 606/176
4,702,236 10/1987 Tarabichy et al. ................... 606/86

FOREIGN PATENT DOCUMENTS 2427716 11/1975 Fed. Rep. of Germany ........ 606/82

Primary Examiner—Mickey Yu
Assistant Examiner—Kevin G. Rooney
Attorney, Agent, or Firm—Fleit, Jacobson, Cohn, Price, Holman & Stern

[57] ABSTRACT

The removal of prosthetic cement from the medullary canal of a patient's long bone such as the femur during replacement of a joint prosthesis. The process comprises the steps of: (a) determining by X-ray or CT scan the profile of a line of intersection of a longitudinal plane, which extends longitudinally through the bone, the prosthetic cement and a prosthetic cavity therein, and a cement/bone interface; (b) determining the thickness of the prosthetic cement in the phase and along the line from the X-ray or CT scan; (c) forming a substantially planar cutting blade with a cutting edge having a profile substantially corresponding to the profile of the line; (d) forming on the cutting blade depth limiting members which are spaced from adjacent points on the cutting edge by a distance substantially equal to the depth of the prosthetic cement at the corresponding points along the plane; (e) inserting the cutting blade into the prosthetic cavity with the blade lying in the plane and to a depth such that corresponding points on the cutting edge are adjacent corresponding points on the line; (f) causing the cutting edge to reciprocate; (g) cutting into the prosthetic cement with the blade until the depth limiting members engage with the surface of the prosthetic cavity adjacent the plane; (h) repeating steps (a) to (g) to form at least one other cut through the prosthetic cement and (i) removing the segments of prosthetic cement so formed from the medullary canal of the bone. The process allows easier and faster removal of the prosthetic cement during joint prosthesis replacement with reduced possibility of bone damage.

9 Claims, 4 Drawing Sheets

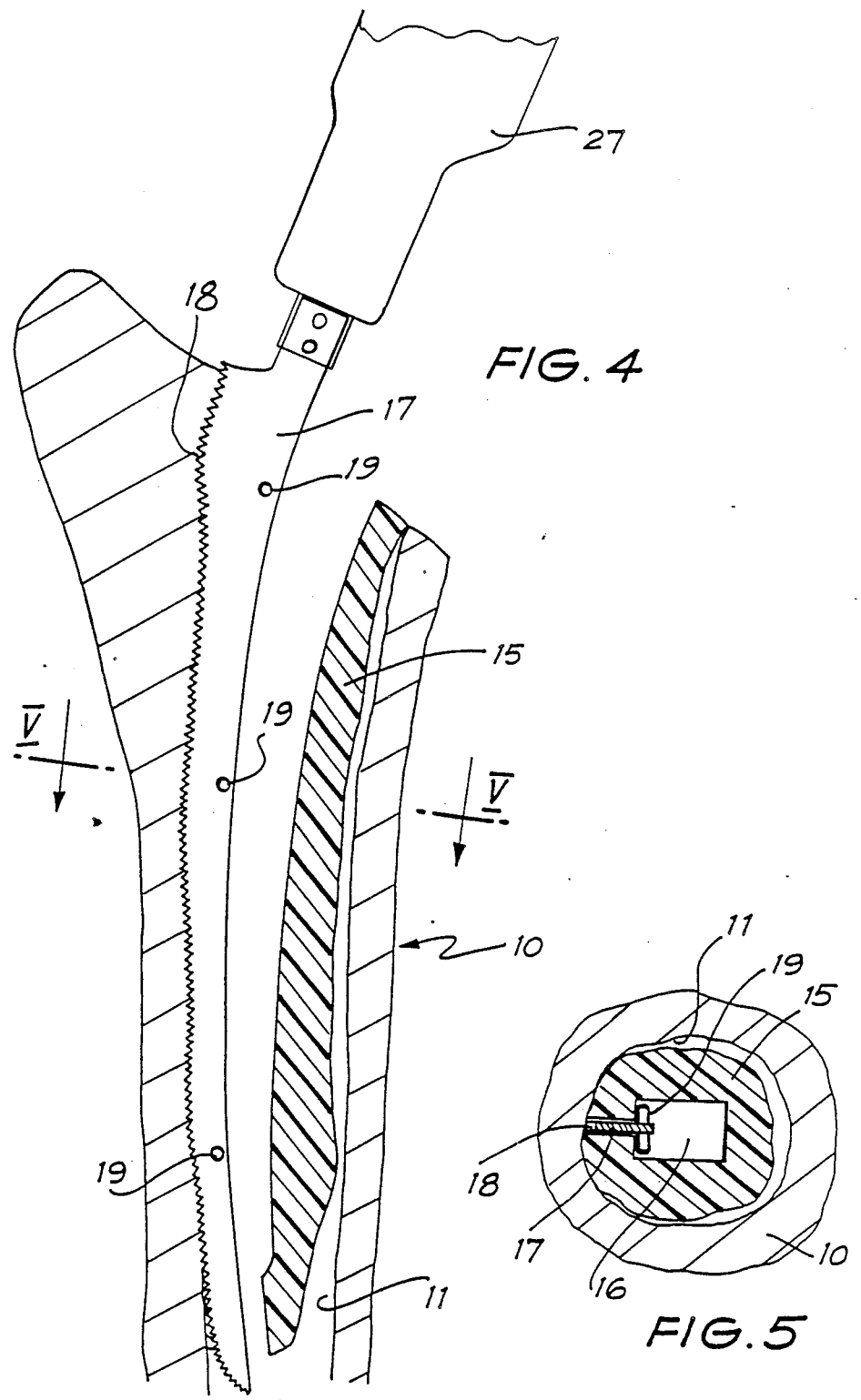

METHOD AND APPARATUS FOR REMOVING PROSTHETIC CEMENT

TECHNICAL FIELD

The present invention relates to an improved process for the removal of prosthetic cement from the medullary canal of a patient's long bone during the replacement of a joint prosthesis, and to a cutting blade for use therein.

BACKGROUND ART

The present inventor has proposed in PCT patent application PCT/AU86/00321 that the removal of prosthetic cement from the medullary canal of a patient's long bone can be facilitated during a joint prosthesis replacement operation by making two or more longitudinally extending cuts through the bone cement after removal of the old prosthesis. These cuts divide the originally tubular bone cement into a number of segments which may be conveniently levered away from the associated bone and removed from the medullary canal. In the aforementioned patent application means were described for forming such cuts through the prosthetic cement substantially without cutting into the underlying bone. These means included guide means to guide a saw blade along the line of intersection of a longitudinal plane extending through the bone, the prosthetic cement and a prosthetic cavity therein and a bone/prosthetic cement interface intersected by the plane.

DISCLOSURE OF THE INVENTION

The present inventor has now discovered that these guide means may be dispensed with if a cutting blade with a suitably profiled cutting edge is provided with depth limiting means which can bear against the surface of the prosthetic cavity adjacent the said plane to limit the depth to which the blade can cut into the prosthetic cement along the plane to the depth of the prosthetic cement along that plane.

The present invention thus consists in a process for the removal of prosthetic cement from the medullary canal of a patient's long bone during replacement of a joint prosthesis, comprising the steps of (a) determining the profile of a line of intersection of a plane, which extends longitudinally through the bone, the prosthetic cement and a prosthetic cavity therein, and a cement/bone interface intersected by that plane, (b) determining the thickness of the prosthetic cement in the said plane and along the said line, (c) forming a substantially planar cutting blade with a cutting edge having a profile substantially corresponding to the profile of the line, (d) forming on the cutting blade depth limiting means, the depth limiting means being spaced from adjacent points on the cutting edge by a distance substantially equal to the depth of the prosthetic cement at the corresponding points along the said plane, (e) inserting the cutting blade into the prosthetic cavity with the blade lying in the said plane and to a depth such that corresponding points on the cutting edge are adjacent corresponding points on the said line, (f) causing the cutting edge to reciprocate, (g) cutting into the prosthetic cement with the blade until the depth limiting means engage with the surface of the prosthetic cavity adjacent the said plane, (h) repeating steps (a) to (g) to form at least one other cut through the prosthetic cement, and (i) removing the segments of prosthetic cement so formed from the medullary canal.

In another aspect the present invention consists in a cutting blade for use in the removal of prosthetic cement from the medullary canal of a patient's long bone during the replacement of a joint prosthesis, comprising a substantially planar blade having a cutting edge, the edge having a profile substantially corresponding to the profile of the line of intersection of a plane, which extends longitudinally through the long bone, the prosthetic cement and a prosthetic cavity therein, and a cement/bone interface intersected by that plane, and cutting depth limiting means on the blade, the depth limiting means being spaced from an adjacent point on the cutting edge by a distance substantially equal to the depth of the prosthetic cement at the corresponding point along the said plane.

The blade is preferably formed with saw teeth along the cutting edge. The depth limiting means may comprise a rib extending along the length of the blade or, more preferably, a series of stops spaced apart along the length of the blade. In a particularly preferred embodiment of the invention the depth limiting means comprises three pegs secured in holes in the blade and each projecting slightly on either side of the blade. It is preferable that at least two, more preferably at least three and most preferably four cuts are made through the prosthetic cement. The cuts are preferably equiangularly disposed around the prosthetic cavity.

The process and the cutting blade according to this invention are particularly suitable for use in replacement hip prosthetic operations in which an old prosthesis is removed from the femur and replaced with a new prosthesis.

BRIEF DESCRIPTION OF THE DRAWINGS

FIG. 4 is a vertical sectional view through the femur of FIG. 3 with a reciprocating saw blade in position after having made a saw cut through the prosthetic cement; and FIG. 5 is a transverse sectional view along V—V of FIG. 4.

BEST MODE OF CARRYING OUT THE INVENTION

Figure 1:
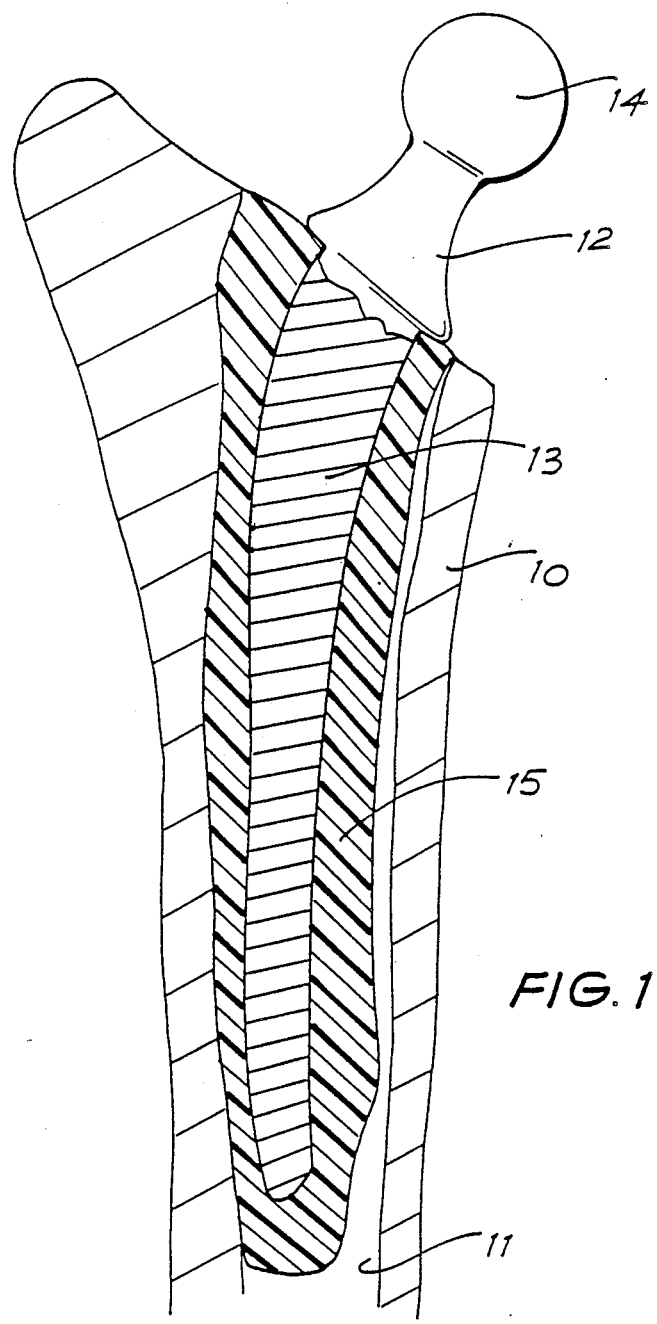
FIG. 1 is a vertical sectional view through a femur into which an artificial hip prosthesis has been fixed.

The invention is hereinafter described for the replacement of the femoral part of a total hip replacement prosthesis with reference to the drawings hereinbefore identified.

The femur 10 of a patient has in the medullary canal 11 a hip prosthesis 12 comprising a stem 13 and head 14. The prosthesis 12 was originally firmly held in place in the medullary canal 11 by prosthetic cement 15 comprising polymethyl methacrylate. Over time the prosthesis 12 and the cement 15 have worked loose in the medullary canal 11 of the femur 10.

The hip prosthesis 12 can usually be easily removed from the cement 15 by pulling the prosthesis 12 longitudinally of the bone. The withdrawn stem 13 leaves a cavity 16 in the cement 15. The problem then remains of how to remove the cement 15 without damaging the bone 10.

In the process according to this invention the patient is, prior to removal of the old prosthesis, examined using X-rays or a CT scanner. If X-ray examination is used one X-ray photograph is taken from the front and one from the side of the patient to define the geometry of the stem 13 relative to the bone 10 along two defined planes and thus the configuration of the cement 15 along these same planes. The CT examination can also provide this information.

Figure 2:
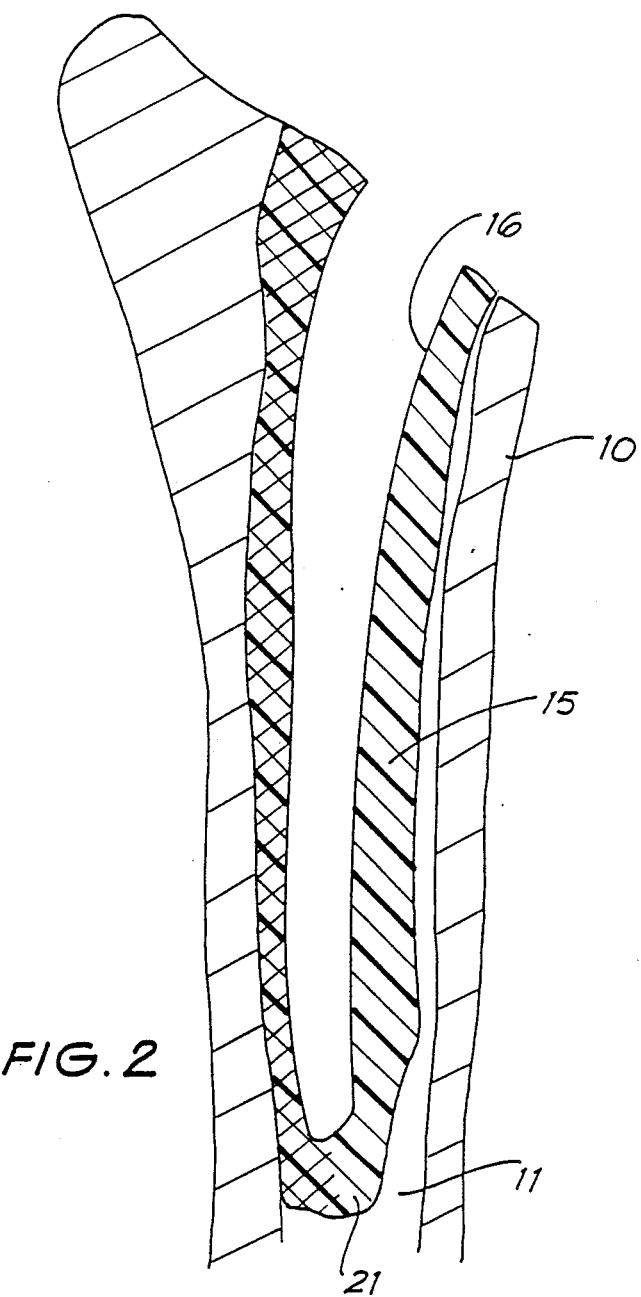
FIG. 2 is a vertical sectional view through the femur of FIG. 1 with the prosthesis removed and showing by cross hatching an area of the prosthetic cement to be removed by sawing.
Figure 3:
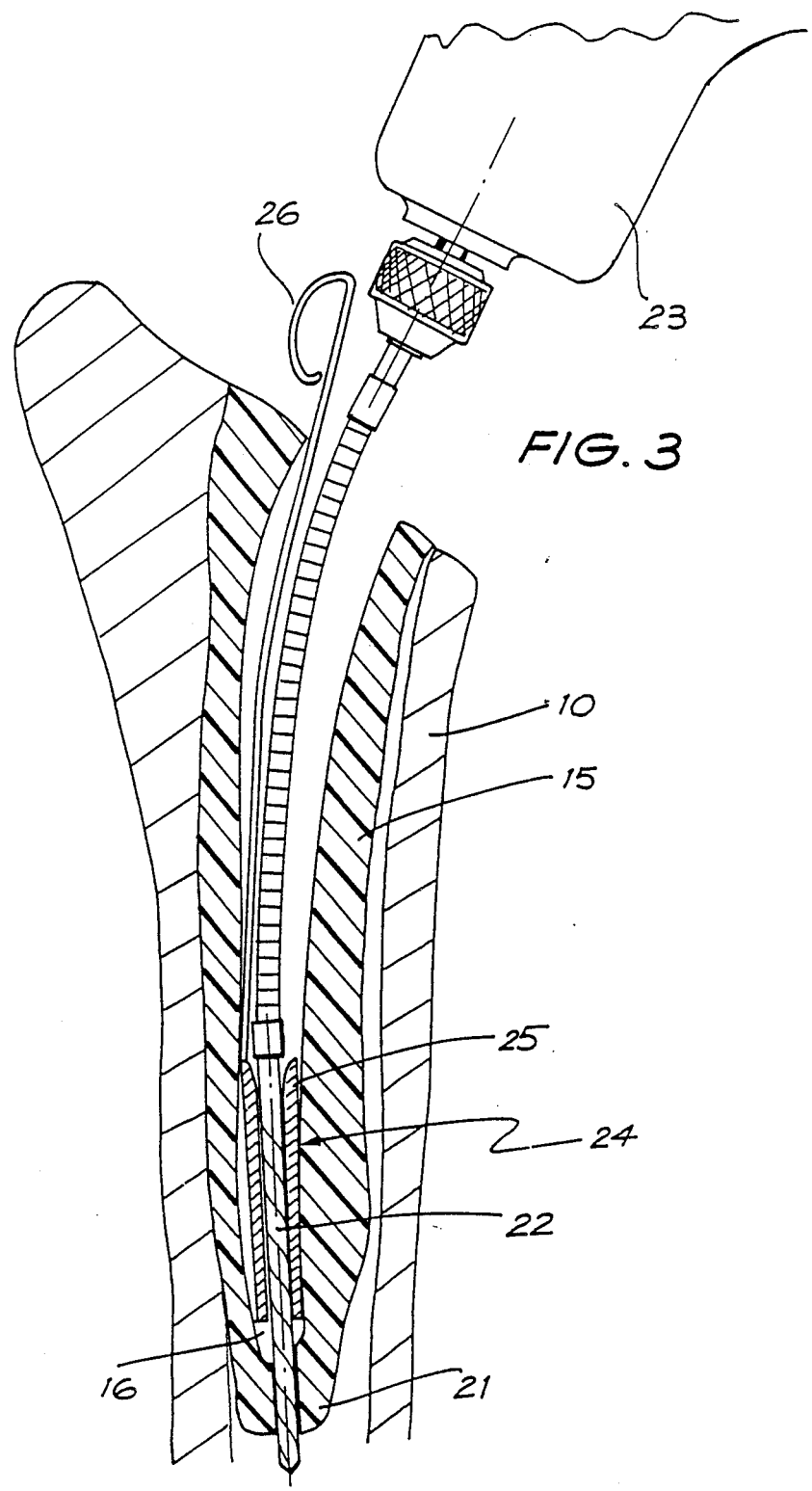
FIG. 3 is a vertical sectional view through the femur of FIG. 2 showing the base of the prosthetic cement being drilled out.

The thickness of the cement 15 is measured along the above planes by examination of the X-ray photographs or CT scan. The thickness of one cut through cement 15 is shown by cross-hatching in FIG. 2. Appropriate jig saw blades 17 can then be made each having a cutting edge profile 18 corresponding to the profile of the cement 15 bone 10 interface along one of the defined planes and each having projections 19 spaced from the cutting edge 18 of the blade 17 by a distance corresponding to the thickness of the cement 15 adjacent the stop means 19 along that plane.

The saw blades 17 are preferably cut using a computer guided laser mill. If desired computer aided design (CAD) software may be used to transform the X-ray images or the CT scan directly into instructions for the laser mill. The projection 19 may be formed by drilling holes at appropriate positions on each blade 17 and inserting a small rod through each hole such that each rod projects slightly on each side of the blade 17 and securing it in position in the blade as by welding.

Once the old prosthesis 12 has been withdrawn from the femur 10 a hole is drilled in the blind end 21 of the prosthetic cement 15 using a flexible drill bit 22 driven by an electric or pneumatic drill 23 and guided by a drill guide 24. The drill guide 24 comprises a tapered tube 25 adapted to fit within the recess 16 in the cement 15 left by withdrawal of the prosthesis and a handle 26. After the drill guide is positioned within the recess 16 adjacent the blind end 21 the drill bit is inserted into the drill guide 24 and used to drill a hole through the blind end 21 of the cement.

The saw blade 17 is then attached to a pneumatically driven reciprocating saw (partly shown at 27) and inserted into the recess 16. The saw blade 17 should be aligned in the correct plane and be inserted to the correct depth and then caused to cut into the cement 15. The projections 19 will abut against the inside surface of the cement 15 when the saw blade 17 has cut through the full thickness of the cement 15.

If the saw blade 17 is too wide to fit within the recess 16 a preliminary, shallow, cut may be made with a second saw blade (not shown) to allow the insertion of saw blade 17.

Once the cut with saw blade 17 is completed the procedure is repeated a further three times to cut the cement 15 into four segments. Each of these four segments can then be readily levered away from the femur 10 and withdrawn longitudinally from the medullary canal.

In practice it has been found that a slight cutting into the bone 10 beneath the cement 15 is acceptable. This permits the use of a pre-formed set of saw blades having shapes corresponding to internal shapes commonly found in femurs. A surgeon may select from such a preformed set the saw blade which has the best fit for each of the particular cuts which is to be made on a particular patient. It is to be understood that the use of such a preformed saw blade is encompassed within the scope of the present invention.

I claim:

1. A process for the removal of prosthetic cement from the medullary canal of a patient's long bone during replacement of a joint prosthesis, comprising the steps of (a) determining the profile of a line of intersection of a plane, which extends longitudinally through the bone, the prosthetic cement and a prosthetic cavity therein, and a cement/bone interface intersected by that plane, (b) determining the thickness of the prosthetic cement in the said plane and along the said line, (c) forming a substantially planar cutting blade with a cutting edge having a profile substantially corresponding to the profile of the line, (d) forming on the cutting blade depth limiting means, the depth limiting means being spaced from adjacent points on the cutting edge by a distance substantially equal to the depth of the prosthetic cement at the corresponding points along the said plane, (e) inserting the cutting blade into the prosthetic cavity with the blade lying in the said plane and to a depth such that corresponding points on the cutting edge are adjacent corresponding points on the said line, (f) causing the cutting edge to reciprocate, (g) cutting into the prosthetic cement with the blade until the depth limiting means engage with the surface of the prosthetic cavity adjacent the said plane, (h) repeating steps (a) to (g) to form at least one other cut through the prosthetic cement, and (i) removing the segments of prosthetic cement so formed from the medullary canal.

2. A process as claimed in claim 1 in which at least three cuts are formed in the prosthetic cement along three separate planes.

3. A process as claimed in claim 2 in which the cuts are substantially equiangularly spaced around the prosthetic cavity.

4. A process as claimed in claim 3 in which a preliminary cut partially through the thickness of the prosthetic cement along the said plane is made before step (e) to allow for the insertion into the prosthetic cavity of a cutting blade wide enough to cut through the full thickness of the prosthetic cement on that plane.

5. A cutting blade for use in the removal of prosthetic cement from the medullary canal of a patient's long bone during the replacement of a joint prosthesis, comprising a substantially planar blade having a cutting edge, the edge having a profile substantially corresponding to the profile of the line of intersection of a plane, which extends longitudinally through the long bone, the prosthetic cement and a prosthetic cavity therein, and a cement/bone interface intersected by that plane, and cutting depth limiting means on the blade, the depth limiting means being spaced from an adjacent point on the cutting edge by a distance substantially equal to the depth of the prosthetic cement at the corresponding point along the said line.

6. A cutting blade as claimed in claim 5 in which the cutting blade is formed along its cutting edge with saw teeth.

7. A cutting blade as claimed in claim 5 in which the depth limiting means comprises a rib extending along the length of the cutting blade.

8. A cutting blade as claimed in claim 5 in which the depth limiting means comprises a series of stop members spaced apart along the length of the cutting blade.

9. A cutting blade as claimed in claim 8 in which the depth limiting means comprises three pegs secured in holes in the cutting blade and projecting slightly from either side of the blade.

* * * * *